(12) United States Patent
Brown et al.

(10) Patent No.: US 11,790,329 B2
(45) Date of Patent: *Oct. 17, 2023

(54) SYSTEM FOR PROCESSING RETAIL CLINIC CLAIMS

(71) Applicant: MedImpact Healthcare Systems, Inc., San Diego, CA (US)

(72) Inventors: Dale R. Brown, Poway, CA (US); William J. Barre, Escondido, CA (US); Frederick Howe, Rancho Santa Fe, CA (US)

(73) Assignee: MedImpact Healthcare Systems, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/888,880

(22) Filed: Aug. 16, 2022

(65) Prior Publication Data

US 2022/0391858 A1 Dec. 8, 2022

Related U.S. Application Data

(63) Continuation of application No. 16/773,847, filed on Jan. 27, 2020, now Pat. No. 11,507,927, which is a
(Continued)

(51) Int. Cl.
*G06Q 20/04* (2012.01)
*G06Q 10/087* (2023.01)
(Continued)

(52) U.S. Cl.
CPC .......... *G06Q 20/04* (2013.01); *G06Q 10/087* (2013.01); *G06Q 10/10* (2013.01); *G06Q 20/14* (2013.01);
(Continued)

(58) Field of Classification Search
CPC ...... G06F 19/328; G16H 80/00; G06Q 40/08; G06Q 50/22
See application file for complete search history.

(56) References Cited

U.S. PATENT DOCUMENTS

| 5,301,105 A | 4/1994 | Cummings, Jr. |
| 5,704,044 A | 12/1997 | Tarter et al. |

(Continued)

FOREIGN PATENT DOCUMENTS

| WO | 9524010 A1 | 9/1995 |
| WO | 9744752 A1 | 11/1997 |

OTHER PUBLICATIONS (Oct. 27, 2006) Bank of America and Caremark introduce pharma rewards credit card, http://www.banking-business-review.com/news/bank_of_america_and_caremark_introduce_pharma_r, 1 Page.
(Continued)

*Primary Examiner* — Joseph D Burgess
(74) *Attorney, Agent, or Firm* — Mintz, Levin, Cohn, Ferris, Glovsky and Popeo, P.C.

(57) ABSTRACT

A method for electronically determining patient medical treatment eligibility, coverage, copayment amount and insurer billing simultaneously, by: (a) a patient requesting medical treatment at a retail clinic; (b) the patient presenting a health insurance card at the retail clinic; (c) the retail clinic transmitting patient health insurance card information to a centralized adjudication facility; (d) the retail clinic transmitting medical treatment information to the centralized adjudication facility; (e) the centralized adjudication facility determining patient medical treatment coverage, eligibility and copayment amount (f) transmitting the patient medical treatment coverage, eligibility and copayment amount from the centralized adjudication facility to the retail clinic; (g) the patient purchasing the medical treatment by paying the retail clinic the copayment amount, (h) transmitting a bill to
(Continued)

the health care insurance provider; and (i) thereby informing the retail clinic clinician to sell the medical treatment to the patient.

20 Claims, 4 Drawing Sheets

Related U.S. Application Data continuation of application No. 15/948,898, filed on Apr. 9, 2018, now abandoned, which is a continuation of application No. 12/390,790, filed on Feb. 23, 2009, now abandoned.

(51) Int. Cl.
 G06Q 20/14 (2012.01)
 G06Q 40/08 (2012.01)
 G06Q 10/10 (2023.01)
 G06Q 50/22 (2018.01)
 G16H 40/20 (2018.01)
 G16H 10/60 (2018.01)

(52) U.S. Cl.
 CPC ............. *G06Q 40/08* (2013.01); *G06Q 50/22* (2013.01); *G16H 10/60* (2018.01); *G16H 40/20* (2018.01)

(56) References Cited

U.S. PATENT DOCUMENTS

| | | | |
|---|---|---|---|
| 5,737,539 A | 4/1998 | Edelson et al. | |
| 5,845,255 A | 12/1998 | Mayaud | |
| 6,108,635 A | 8/2000 | Herren et al. | |
| 6,195,612 B1 | 2/2001 | Pack-harris | |
| 6,283,761 B1 | 9/2001 | Joao | |
| 6,341,265 B1* | 1/2002 | Provost ................ | G16H 50/20 705/4 |
| 7,165,077 B2 | 1/2007 | Kalies | |
| 7,412,396 B1 | 8/2008 | Haq | |
| 7,490,047 B2 | 2/2009 | Brown et al. | |
| 7,505,917 B2 | 3/2009 | Howe et al. | |
| 7,685,026 B1 | 3/2010 | Mcgrady et al. | |
| 7,949,580 B1* | 5/2011 | Boyer ................. | G06Q 20/18 705/35 |
| 8,060,379 B1 | 11/2011 | Pinsonneault et al. | |
| 8,069,059 B2 | 11/2011 | Howe et al. | |
| 8,099,295 B2 | 1/2012 | Virdee et al. | |
| 8,265,950 B2 | 9/2012 | Howe et al. | |
| 8,346,571 B2 | 1/2013 | Kalies, Jr. | |
| 2001/0037216 A1 | 11/2001 | Oscar et al. | |
| 2002/0002495 A1 | 1/2002 | Ullman | |
| 2002/0049617 A1 | 4/2002 | Lencki et al. | |
| 2002/0082863 A1 | 6/2002 | Kleinke | |
| 2002/0095316 A1 | 7/2002 | Toan et al. | |
| 2002/0111832 A1 | 8/2002 | Judge | |
| 2002/0120473 A1 | 8/2002 | Wiggins | |
| 2002/0147617 A1 | 10/2002 | Schoenbaum et al. | |
| 2002/0169727 A1 | 11/2002 | Melnick et al. | |
| 2002/0183965 A1 | 12/2002 | Gogolak | |
| 2003/0154106 A1 | 8/2003 | Marks | |
| 2003/0195771 A1 | 10/2003 | Fitzgerald et al. | |
| 2004/0054685 A1 | 3/2004 | Rahn et al. | |
| 2004/0073457 A1 | 4/2004 | Kalies | |
| 2004/0133452 A1 | 7/2004 | Denny et al. | |
| 2004/0143171 A1 | 7/2004 | Kalies | |
| 2004/0148194 A1 | 7/2004 | Wellons et al. | |
| 2004/0148195 A1 | 7/2004 | Kalies | |
| 2004/0148196 A1 | 7/2004 | Kalies | |
| 2004/0148198 A1 | 7/2004 | Kalies | |
| 2004/0148203 A1 | 7/2004 | Whitaker et al. | |
| 2004/0230502 A1 | 11/2004 | Fiacco et al. | |
| 2005/0060188 A1 | 3/2005 | Valley | |
| 2005/0065821 A1 | 3/2005 | Kalies, Jr. | |
| 2005/0071193 A1 | 3/2005 | Kalies | |
| 2005/0071200 A1 | 3/2005 | Franklin et al. | |
| 2005/0240442 A1 | 10/2005 | Lapsker | |
| 2005/0251429 A1 | 11/2005 | Ammer et al. | |
| 2005/0261939 A1 | 11/2005 | Augspurger et al. | |
| 2005/0283259 A1 | 12/2005 | Wolpow | |
| 2006/0020514 A1 | 1/2006 | Yered | |
| 2006/0116905 A1 | 6/2006 | Yered | |
| 2006/0129357 A1 | 6/2006 | Francis et al. | |
| 2006/0178915 A1 | 8/2006 | Chao | |
| 2006/0184391 A1 | 8/2006 | Barre et al. | |
| 2006/0271402 A1 | 11/2006 | Rowe et al. | |
| 2007/0005402 A1 | 1/2007 | Kennedy et al. | |
| 2007/0011025 A1 | 1/2007 | Cracchiolo et al. | |
| 2007/0050210 A1 | 3/2007 | Wiley | |
| 2007/0106623 A1 | 5/2007 | Melnick et al. | |
| 2007/0168234 A1 | 7/2007 | Rutkowski et al. | |
| 2007/0250341 A1 | 10/2007 | Howe et al. | |
| 2008/0312956 A1 | 12/2008 | Momita et al. | |
| 2009/0076868 A1 | 3/2009 | Malone et al. | |
| 2009/0144082 A1 | 6/2009 | Selbst et al. | |
| 2009/0177488 A1 | 7/2009 | Unland et al. | |
| 2009/0177490 A1 | 7/2009 | Howe et al. | |
| 2009/0281823 A1 | 11/2009 | Hardaway | |
| 2009/0281824 A1 | 11/2009 | Hardaway | |
| 2009/0319311 A1 | 12/2009 | Mi et al. | |
| 2009/0326975 A1 | 12/2009 | Hardaway et al. | |
| 2010/0057489 A1 | 3/2010 | Howe et al. | |
| 2010/0161351 A1 | 6/2010 | Howe et al. | |
| 2010/0217622 A1 | 8/2010 | Brown et al. | |
| 2010/0287002 A1 | 11/2010 | Barre et al. | |
| 2010/0312578 A1 | 12/2010 | Hardaway | |
| 2011/0029321 A1 | 2/2011 | Rourke et al. | |
| 2011/0054935 A1 | 3/2011 | Hardaway | |
| 2019/0050829 A1 | 2/2019 | Brown et al. | |
| 2020/0364679 A1 | 11/2020 | Brown et al. | |

OTHER PUBLICATIONS (May 11,2006) CitiBusiness Credit Cards Free Prescription Discount Program, 07:14 AM Pacific http://www. paymentsnews.com/2006/05/citibusiness_cr.html, 3 Pages.

(May 11,2006) CitiBusiness(R) Credit Cards Announces New Card member Benefit Free Prescription Discount Program, http:/Mw-N. prnewswire.com/cgi-bin/stories.pl?ACCT=104&STORY=/ww, 2 Pages.

(Nov. 24, 2006) Comments of Generic Pharmaceutical Association for the Public Meeting on Proposed Changes to the National Drug Code System, RIN 0910-AA49, 7 Pages.

Jul. 5, 2001) Cost Sharing Strategies for OHP Medical Services, 1-5 Pages.

(Mar. 26, 2008) Credit Cards Offer Discounts on Prescription Drugs, http://wbztv.com/consumer/credit.Card.Discounts.2.682345. html, 2 Pages.

LNFOCROSSING (2007) "Prescription Drug Event (PDE) Submission Process Summary", Infocrossing Healthcare Services, Inc, 2 Pages.

(Jul. 14, 2006) CVS to Buy MinuteClinic Walk-In Medical Service, Los Angeles Times, 1 Page.

(Apr. 27, 2006) Department of Health and Human Services, Requirements for Submitting Prescription Drug Event, Centers for Medicare and Medicaid Services, 92 Pages.

(2008) Florida House of Representatives, Enrolled CS/HB 535, Legislature, 5 Pages.

International Search Report and Written Opinion received for International Application No. PCT/US06/42976, dated Sep. 11, 2007, 9 Pages.

Lipton et al. (Mar.-Apr. 2000) "Managing The Pharmacy Benefit in Medicare HMOs: What Do We Really Know?", Health Affairs, 19(2):42-58.

(Mar. 25, 2008) Medimpact Medicare Part D 2008 Pre-Processing Drug List (PPDL) White Paper, 5 Pages.

(Mar. 25, 2008) Medimpact Medicare Part D 2009 Pre-Processing Drug List (PPDL) White Paper, 5 Pages.

(Oct. 13, 2005) Medimpact Medicare Part D Drug List White Paper, 4 Pages.

(56) References Cited

OTHER PUBLICATIONS (Jul. 20, 2006) Medimpact Medicare Part D Pre-Processing Drug List (PPDL) White Paper, 5 Pages.
(Jun. 6, 2009) Prescription Card, Available on: https://www.unionplus.org/benefits/health/prescriptions, 2 Pages.
(Nov. 9, 2005) Systems Xcellence Announces Three-Year $4.0 Million Software License, Support and Operations Contract, 2 Pages.
Laing et al. (Feb. 2007) "Tuberculosis Drug Issues: Prices, Fixed Dose Combination Products and Second Line Drugs", Journal Tuberculosis Disease, 4(12):S194-S207.
(Jun. 10, 2009) Walgreens Store Green Dot Prepaid MasterCard and Visa cards, Available on: http://www.walgreens.com/store/promotion/greendot/default.jsp, 2 Pages.
Huskamp et al. (Mar.-Apr. 2000) "The Medicare Prescription Drug Benefit: How Will the Game be Played?", Health Affairs, 19(2):8-23.
Federal Register (May 16, 2008) "Medicare Program; Revisions to the Medicare Advantage and Prescription Drug Benefit Programs", Department of Health and Human Services (Hhs), (FIND73.096), 30 Pages.
Hubers et al. (1996) "Credit Card System Solves Problem of Collecting on Co-Payments", Los Angeles Business Journal, 1 Page.

\* cited by examiner

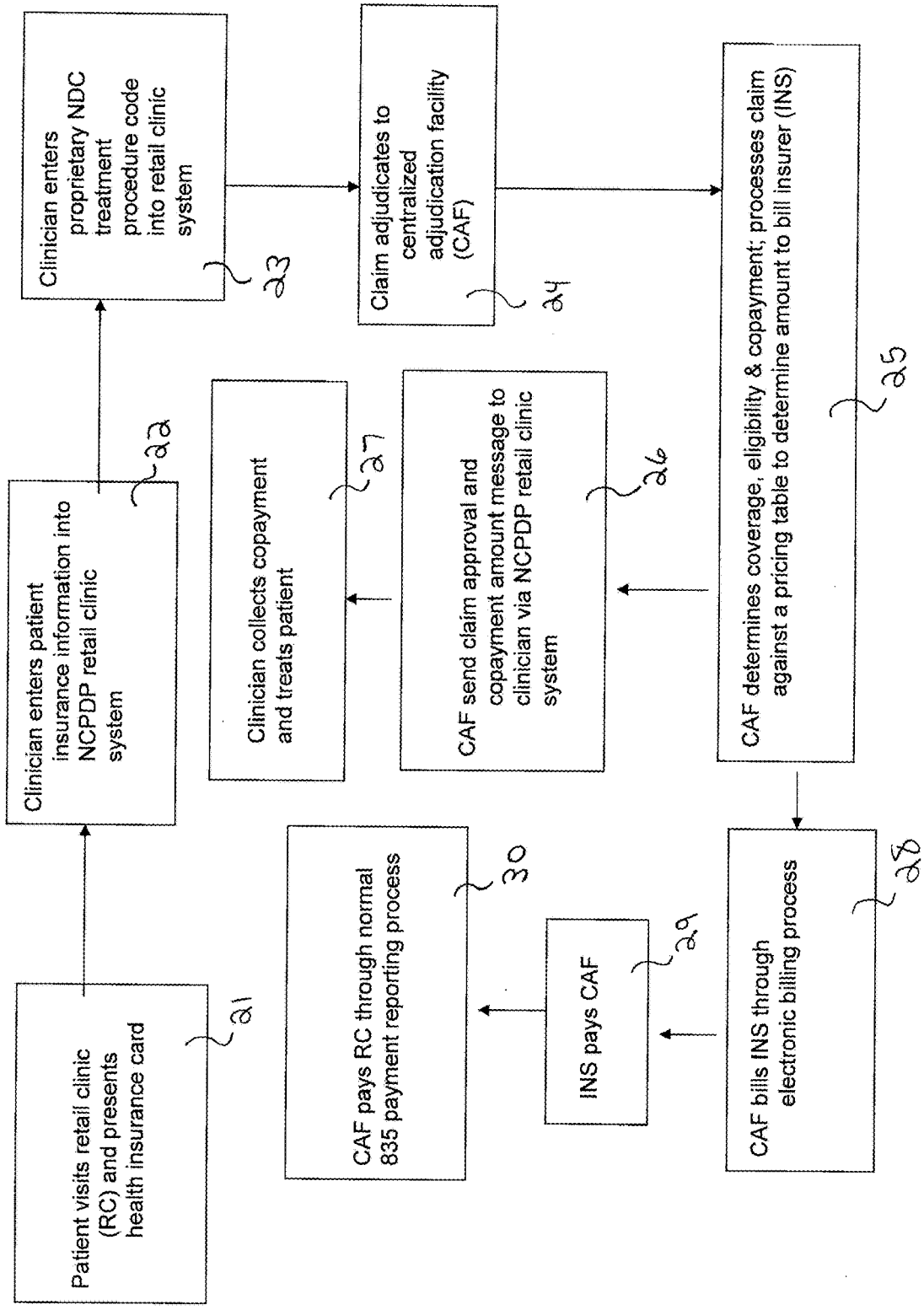
Figure 2: Claim information entered into NCPDP retail clinic system process

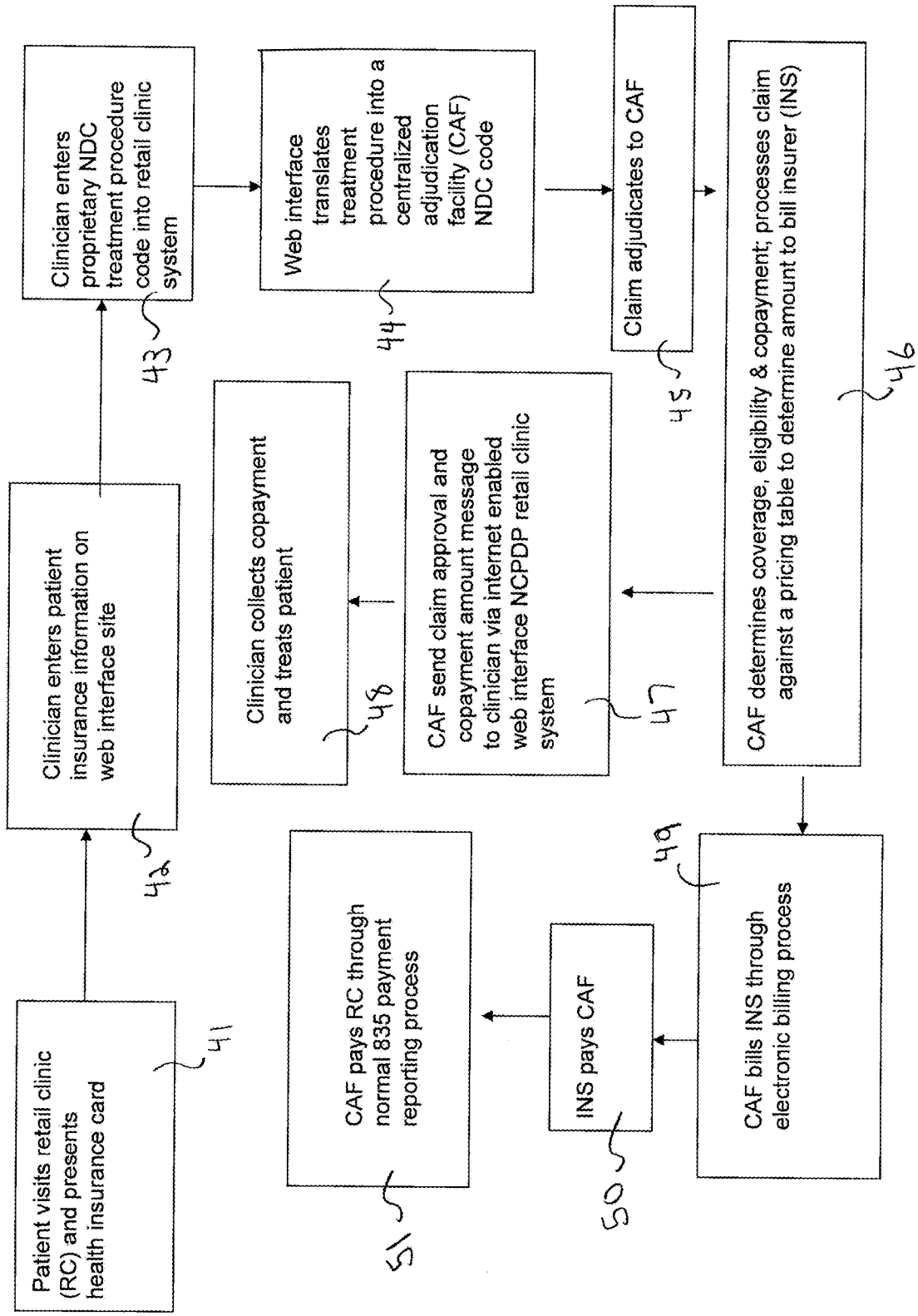
Figure 3: Claim information entered into Internet enabled web interface NCPDP retail clinic system process

Figure 4: Financial card process
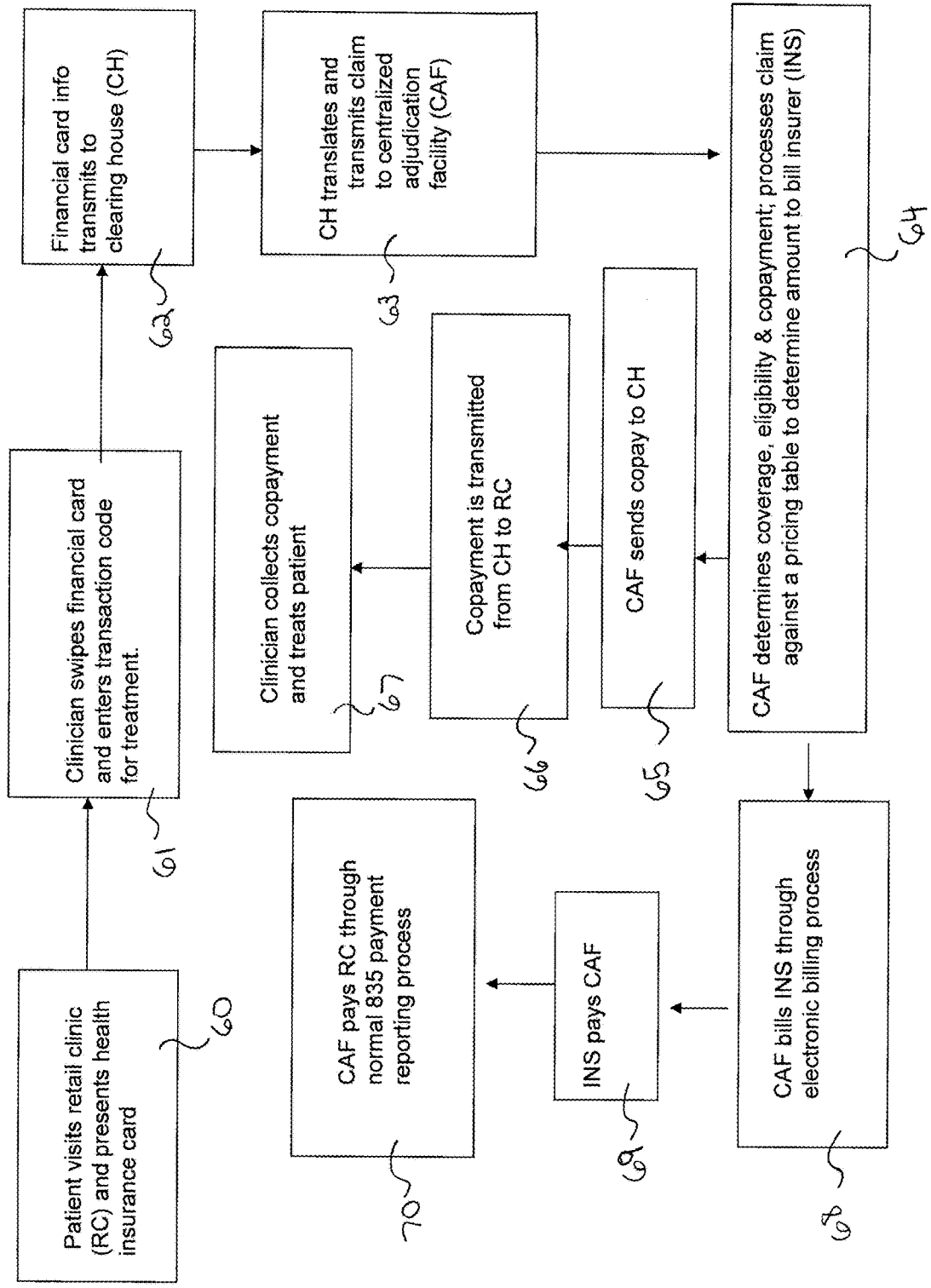

SYSTEM FOR PROCESSING RETAIL CLINIC CLAIMS

CROSS-REFERENCES TO RELATED APPLICATIONS

This application is a continuation of U.S. patent application Ser. No. 16/773,847 filed on Jan. 27, 2020, granted as U.S. Pat. No. 11,507,927, entitled "SYSTEM FOR PROCESSING RETAIL CLINIC CLAIMS," which is a continuation of U.S. patent application Ser. No. 15/948,898 filed on Apr. 9, 2018, which is a continuation of U.S. patent application Ser. No. 12/390,790 filed on Feb. 23, 2009, the entire contents of each are hereby incorporated herein by reference in their entireties and for all purposes.

TECHNICAL FIELD

The present application relates to systems for adjudicating patient medical claims in retail clinics.

BACKGROUND

The retail medical or convenient care clinic industry began in 2000. Retail clinics are staffed by nurse practitioners, registered nurses, physician assistants and physicians. The consumer (patient) is provided access to convenient medical care (e.g.: flu shots, treating ear infections, etc.) performed at the retail clinics which are found inside pharmacies, supermarkets, big-box retailers and independently operated retail spaces. These retail clinics are either owned directly by the retailer, leased spaced within the store or are operated in partnership with a local community healthcare entity. Retail clinics work with health care insurance providers, but insurance coverage for medical treatments depends on the insurer, the clinic's company and the state. Despite coordination between the retail clinic and insurer (i.e.: the health care insurance provider), clinicians at retail clinics do not have real-time or online access to insurer data. As a result, there is confusion at the point of sale determining patient medical treatment coverage, eligibility, copayment amount and insurer cost.

Typically, a patient walks into a retail clinic, signs in and indicates the medical treatment required. The clinician at the retail clinic asks the patient for his/her health insurance card which identifies the patient's health plan coverage. Next, the clinician reviews information about the patient's health care plan to determine coverage and eligibility. This is typically done by manually reviewing plan summary sheets, checking the Internet and/or by making telephone calls to the plan administrators.

This process is inefficient and flawed. The clinician may unknowingly make an inaccurate determination of patient coverage, eligibility or copayment amount and is unable to conclusively resolve with the information available to him/her. In this case, the clinician may make a "note" that a patient was treated with the intention of coming back later to confirm the transaction, and enter a final record of the medical treatment into the retail clinic computer system. Unfortunately, the clinician may not have enough time to research and record the full transaction (especially if many patients are waiting in line). The clinician may then finish his/her working shift and leave, with the computer having multiple "post-it" notes attached to it for the next clinician to attempt to reconcile.

The above problems are further complicated by the fact that retail clinics are staffed by only a few (or typically one) clinician.

SUMMARY

The present application provides an efficient and accurate system for retail clinics to determine patient medical treatment coverage, eligibility, copayment amount and insurer cost. Rather than have the transaction treated as a medical claim, which requires post-treatment billing, and is slow and cumbersome through use of the paper and mail based billing, the patient and insurer billing is electronically processed.

In one preferred aspect, the present application provides a method to determine patient medical treatment coverage, eligibility, copayment amount and insurer cost. In preferred aspects, the present application involves the steps of:
 (a) a patient requesting medical treatment at a retail clinic;
 (b) the patient presenting a health insurance card at the retail clinic;
 (c) the retail clinic transmitting health insurance card information to a centralized adjudication facility;
 (d) the retail clinic transmitting medical treatment information to the centralized adjudication facility;
 (e) the centralized adjudication facility determining patient coverage, eligibility and copayment amount;
 (f) transmitting the patient medical treatment coverage, eligibility and copayment amount from the centralized adjudication facility back to the retail clinic;
 (g) the patient purchasing the medical treatment by paying the retail clinic the copayment amount;
 (h) transmitting a bill to the health care insurance provider; and
 (i) thereby informing the retail clinic clinician to sell the medical treatment to the patient.

In accordance with the application, the transmission of patient medical treatment coverage, eligibility data and copayment amount from the centralized adjudication facility to the retail clinic enables the clinician to treat the patient. Such retail clinic sales equipment may be comprised of a computer, cash register, financial card swipe machine or some combination thereof. As such, the present method provides a system that transforms the current retail clinic's computer system which does not know what copayment amount to charge the particular patient asking for a particular medical treatment. When the patient medical coverage, eligibility and copayment amount data is sent back to the retail clinic, the retail clinic computer system is activated to complete the sale. This is done by signaling, instructing or otherwise enabling the retail clinic's computer system to adjudicate the transaction and complete the sale. Preferably, the medical treatment coverage, eligibility and copayment amount are displayed on a computer screen at the retail clinic. As such, the retail clinic's computer system is transformed into a state in which it is able to complete the sale of the medical treatment to the patient.

In preferred aspects, the health insurance card information and patient medical treatment information may be transmitted from the retail clinic directly to the centralized adjudication facility over an NCPDP (National Council for Prescription Drug Programs) network. In addition, the medical treatment coverage, eligibility and copayment amount may be transmitted from the centralized adjudication facility back to the retail clinic over the NCPDP retail clinic system. Such data transmission over the NCPDP retail clinic system may be by way of NCPDP standard messaging, or over an Internet enabled web interface NCPDP retail clinic system.

In various aspects, the centralized adjudication facility determines the patient medical treatment coverage and eligibility by identifying the patient on a patient information database. The patient copayment amount may be determined by the centralized adjudication facility by: (i) identifying the medical treatment on a medical treatment database; and then (ii) identifying the patient copayment amount for the medical treatment. In this way, both the requested medical treatment and the patient are identified to determine the particular patient copayment amount that corresponds to that particular patient's health plan coverage.

There are several advantages to this system. First, approval is fast since the clinician in the retail clinic does not spend additional time making the determination. Second, approval decisions are centralized so they are consistent, as a number of different retail clinics may use the same centralized adjudication facility.

The centralized adjudication facility may then directly bill the patient's insurer (for example, by an amount equal to a value of the patient medical treatment less the patient copayment amount). An advantage of this approach is that electronic billing and payment is handled quickly since billing amounts can be simultaneously determined and sent from the centralized adjudication facility to both the patient in the retail clinic and the health care insurance provider.

Thus, the centralized adjudication facility can simultaneously determine what amount the patient is to pay and what amount the insurer is to pay. The retail clinic is then told how much to charge the patient while a bill for the remaining amount of the medical treatment cost is being sent to the insurer. By simultaneously billing the patient and the health care insurance provider, the present application provides a system that processes the sale of the medical treatment as a sales transaction, In some preferred aspects of the application, the health insurance card is a financial credit or debit card such as a VISA™, Master Card™, American Express™, Diner's Club™, or Discover™ card. In this aspect, transmitting health insurance card information to the centralized adjudication facility comprises transmitting the financial card number to the centralized adjudication facility. Alternatively, the financial card number can be transmitted from the retail clinic to a financial clearing house, and then from the financial clearing house to the retail clinic.

An advantage of this financial card approach is that the financial service clearing house (and/or the centralized adjudication facility) may simply identify the patient by the patient's financial card number. Another advantage is that the patient is able to use the same (financial) card as their health insurance card and as the card with which they actually purchase the patient medical treatment. This permits a patient to keep one card in a purse or wallet (as opposed to two).

In some alternate aspects, the centralized adjudication facility may also recommend a substitute medical treatment to the patient.

BRIEF DESCRIPTION OF THE DRAWINGS

FIG. 2 is a flowchart of a preferred method of the present application using standard NCPDP retail clinic system.

FIG. 3 is a flowchart of a preferred method of the present application using an Internet enabled web interface NCPDP retail clinic system.

FIG. 4 is a flowchart showing a preferred method of the present application using a financial services card (e.g.: Visa™ or Master Card™) clearing house.

DETAILED DESCRIPTION OF THE DRAWINGS

Figure 1:
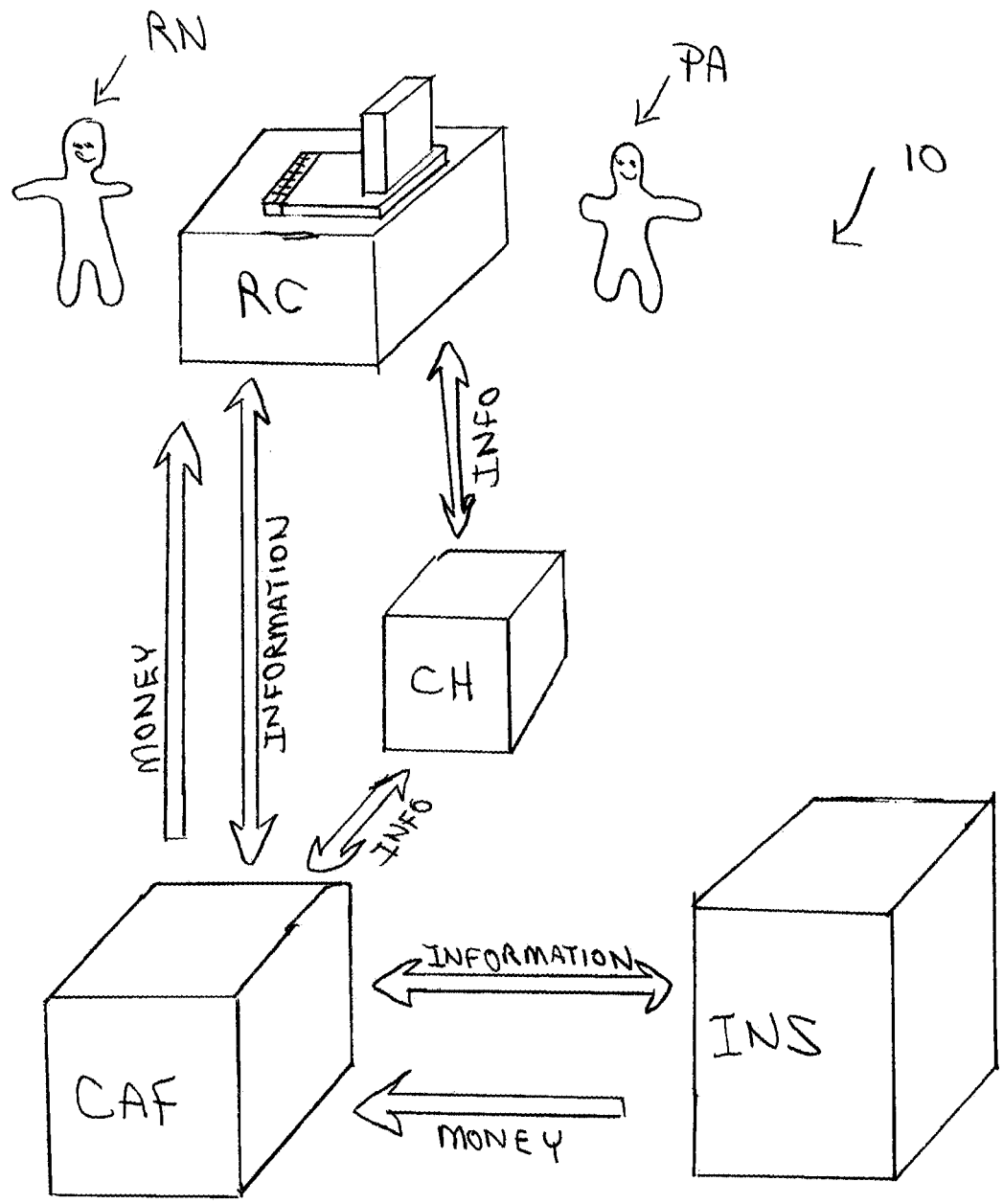
FIG. 1 is a schematic showing the participants, locations of their dedicated retail clinic management hardware and software systems, lines of communication therebetween and financial transfers of the present application during system operation.

FIG. 1 is a schematic illustration of the various participants of the present system. The locations of their hardware systems and the lines of electronic communication between these participants are also shown. Also shown are the directions of financial transfers between the various participants. Not all of the participants shown in FIG. 1 are required in all aspects of the present application. For example, the financial services card clearing house (CH) is optional and is used only in aspects of the embodiments (shown in FIG. 4) where the patient's health insurance card is also a credit or debit card.

The system participants illustrated in FIG. 1 are as follows. System 10 includes a retail clinic (RC), staffed by a clinician (RN). Retail clinics (RC) are found inside pharmacies, supermarkets, big-box retailers and in independently operated retail spaces and are staffed by nurse practitioners, registered nurses, physician assistants and physicians.

A patient (PA) enters a retail clinic (RC), signs into the clinic and indicates the medical treatment they require. The patient is called into the clinicians' office, at which time the patient shows the clinician their health insurance card. As will be explained in detail below, the clinician (RN) uses the retail clinic computer system (and/or financial card swipe machine) to transmit and receive data to a centralized adjudication facility (CAF). Centralized adjudication facility (CAF) then makes the determination of patient coverage, eligibility and copayment amount. That determination information is then transmitted back to the computer and/or the financial card swipe machine located in retail clinic (RC). In the exemplary method of FIGS. 2 and 3, information is transmitted back and forth directly between retail clinic (RC) and centralized adjudication facility (CAF). In the exemplary method of FIG. 4 which uses a financial card, the information is instead transmitted through a financial services card clearing house (CH).

After (or while) determining patient medical coverage, eligibility and copayment amount, the centralized adjudication facility (CAF) then bills insurer (INS). Insurer (INS) then sends funds to centralized adjudication facility (CAF), and centralized adjudication facility (CAF) then sends funds to retail clinic's parent company. As such, retail clinic (RC) is paid for patient medical treatment (with patient (PA) paying their copayment amount, and insurer (INS) paying the remainder of the cost).

The actions (and dedicated retail clinic management equipment) of each of the above participants can be better understood through the process flowcharts of FIGS. 2, 3 and 4, as follows.

Turning first to FIG. 2, a method 20A is provided. Method 20A provides a system for electronically determining coverage, eligibility and billing for retail clinic (RC) patient medical treatment. Method 20A comprises the steps of: step 21, a patient (PA) presents their health insurance card to clinician (RN) and requests medical treatment. Next, at step 22, clinician (RN) enters patient insurance information into a NCPDP retail clinic system. At step 23, clinician (RN) enters a proprietary NDC medical treatment procedure code into the NCPDP retail clinic computer system. As a result, the clinician (RN) has permitted the NCPDP retail clinic system to transmit information identifying both the patient and the medical treatment. This information is needed to determine patient coverage, eligibility and copayment amount. Next, at step 24, the patient health insurance card and the medical treatment information of steps 22 and 23 is transmitted as an electronic claim from retail clinic (RC) to a centralized adjudication facility (CAF). It is to be understood, however that the present system is not limited only to data transmission over NCPDP retail clinic systems. Other retail clinic communication systems are also contemplated within the scope of the present application.

At step 25, the NCPDP retail clinic system transmits information to the centralized adjudication facility (CAF) which determines patient coverage, eligibility and copayment amount for the medical treatment. This may optionally be done by determining copayment amount by processing the claim against a pricing table to determine the amount to bill the insurer. Other options are possible. Centralized adjudication facility (CAF) may determine the patient medical treatment coverage and eligibility by identifying the patient on a patient information database. Centralized adjudication facility (CAF) may determine the patient copayment amount by: (i) identifying the patient medical treatment on a medical treatment database; and then (ii) identifying the patient copayment amount for the medical treatment. This may be done by comparing the patient information database to the medical treatment database to determine the patient copayment amount that corresponds to the patient's health plan coverage.

An advantage of centralized adjudication facility (CAF) is that it may be used for multiple retail clinics, whereby enabling clinicians (RN) in different retail clinics to prevent inaccurate determinations. Another advantage of centralized adjudication facility (CAF) making these determinations is the rapid speed of patient medical treatment approval.

Next, at step 26, centralized adjudication facility (CAF) transmits the patient medical treatment coverage, eligibility and copayment amount back to retail clinic (RC). For example, the centralized adjudication facility (CAF) transmits the patient medical treatment approval (which includes the patient copayment amount) back to retail clinic (RC). This thereby signals the retail clinic computer system to sell the medical treatment to the patient. For example, a message displaying "Camp Physical Approved—Patient copayment is $20" or similar may be displayed on the retail clinic computer screen. Finally, at step 27, clinician (RN) collects the copayment, and treats the patient (PA).

At step 28, centralized adjudication facility (CAF) sends a bill to insurer (INS). In accordance with optional aspects of the present application, steps 26 and 28 may be carried out at the same time or immediately after one another. The advantage of this system is that both the patient and the insurer (INS) are alerted to their respective charges (for the patient medical treatment) at the same time. This will significantly speed up patient medical treatment billing.

Next, at step 29, insurer (INS) transfers funds to centralized adjudication facility (CAF) to pay the bill. Lastly, at step 30, the centralized adjudication facility (CAF) pays retail clinic (RC) for the patient medical treatment. This may preferably be done through a normal NCPDP 835 reporting process. In further optional embodiments, payment for the patient medical treatment may be sent from insurer (INS) directly to retail clinic (RC), all keeping within the scope of the present application. The significant advantage to retail clinics (RC) is that it receives prompt payment for its services (either from centralized adjudication facility (CAF) or from insurer (INS) directly).

Typically, the insurer is billed an amount equal to a value of the patient medical treatment less the patient copayment amount. However, the centralized adjudication facility (CAF) may also charge a service fee to clinic provider and/or health care insurance provider.

The process shown in FIG. 3 is very similar to the process already described with respect to FIG. 2. However, in method 20B illustrated in FIG. 3, clinician (RN) instead uses an Internet enabled web interface NCPDP retail clinic system to send and receive information. The differences between the systems of FIGS. 2 and 3 will now be pointed out. First, at step 41, a patient (PA) presents their health insurance card to clinician (RN) and requests medical treatment. (similar to step 21). Next, clinician (RN) enters patient information on the retail clinic computer system through a web-based interface (somewhat similar to step 22). Next, clinician (RN) enters a proprietary NDC medical treatment procedure code into the NCPDP retail clinic system (somewhat similar to step 23). Next, at step 44, the web interface translates the medical treatment procedure code into a CAF NDC code.

Next, at step 45, the patient health insurance card and patient medical treatment information of steps 42 and 43 is transmitted as a claim from retail clinic (RC) to centralized adjudication facility CAF (similar to step 24). Next, at step 46, the retail clinic computer system transmits information to the centralized adjudication facility (CAF) which determines patient medical treatment coverage, eligibility and copayment amount for the medical treatment (similar to step 25).

Next, at step 47, centralized adjudication facility (CAF) transmits the patient medical treatment coverage, eligibility and copayment amount back to retail clinic (RC), where the information is displayed on the retail clinic computer screen (similar to step 26). Finally, at step 48, clinician (RN) collects the copayment amount, and treats the patient (PA) (similar to step 27).

With regards to billing, step 49 is identical to step 28; step 50 is identical to step 29 and step 51 is identical to step 30.

Finally, FIG. 4 illustrates a method 20C in which a financial card is used. The financial card may be any of a VISA™, Master Card™, American Express™, Discover™ card, or any other retail store specific or health insurance plan specific, or any other form of credit or debit card. In this preferred aspect of the present method, the optional financial services card clearing house (CH) of FIG. 1 is used, as follows.

First, at step 60, patient (PA) presents their health insurance card to clinician (RN) in retail clinic (RC) (similar to steps 21 and 41). Next, at step 61, clinician (RN) swipes the patient's financial card in a financial card swipe machine, and enters the transaction code for the medical treatment. In alternate embodiments, the medical transaction code may be entered (when prompted) into the retail clinic computer, or directly into the financial card swipe machine. Both embodiments are contemplated within the scope of the present application. By entering the financial card number, both the patient and the patient's health care coverage plan can be identified, as will be explained below.

Next, at step 62, the patient financial card and patient medical treatment information of steps 60 and 61 is transmitted from retail clinic (RC) to a financial services clearing house (CH). Next, at step 63, clearing house (CH) translates and transmits a claim to centralized adjudication facility (CAF).

Next, at step 64, the retail clinic computer system transmits information to the centralized adjudication facility (CAF) which determines patient medical treatment coverage, eligibility and copayment amount (similar to steps 25 and 46). At step 65, the centralized adjudication facility (CAF) then sends the patient copayment amount to the clearing house (CH). At step 66, this copayment amount is then transmitted from clearing house (CH) back to the retail clinic (RC). In one embodiment, this copayment amount is displayed on the retail clinic computer screen. In another embodiment, the copayment amount is displayed on the clinician's financial card swipe machine. Then at step 67, the clinician (RN) collects the copayment amount and treats the patient (PA). Alternatively, the copayment amount may be transmitted directly to the financial card swipe machine. This aspect of the application is particularly advantageous in that (for some treatments) the patient may be charged a copayment amount if the medical treatment is covered by their plan, but charged the full amount if medical treatment is not covered by the patient's plan. This is very advantageous since all the patient has to do is swipe their financial card, and the amount that they are charged depends upon their coverage.

With regards to billing, step 68 is identical to steps 28 and 49; step 69 is identical to steps 29 and 50, and step 70 is identical to steps 30 and 51.

Finally, in an additional optional embodiment of the application, applicable to FIG. 2, 3 or 4, the centralized adjudication facility (CAF) may instead recommend a substitute medical treatment to the patient, with the patient then purchasing the substitute medical treatment.

What is claimed is:

1. A computer-implemented method for medical transaction adjudication, the method comprising:
   receiving a patient request for medical treatment;
   receiving health insurance information associated with the patient request;
   transmitting health insurance information to a computer-implemented adjudication system comprising one or more processors for processing the health insurance information;
   transmitting medical treatment information associated with the patient request to the computer-implemented adjudication system; and
   receiving medical treatment coverage, eligibility and copayment amount information associated with the medical treatment from the computer-implemented adjudication system, such that a medical transaction is adjudicated for the requested medical treatment at a point of sale by way of a patient paying a copayment amount to a treatment clinic in real time, and a computing system at the point of sale bills a healthcare insurance provider for the requested medical treatment simultaneous to transmitting data specifying the copayment amount paid by the patient, in response to receiving the medical treatment coverage and eligibility information associated with the requested medical treatment.

2. The method of claim 1, wherein the health insurance information and medical treatment information is transmitted from the treatment clinic to the computer-implemented adjudication system over a National Council for Prescription Drug Programs (NCPDP) network, and in response data about the medical treatment coverage, eligibility and copayment amount are transmitted from the computer-implemented adjudication system to the treatment clinic over the NCPDP network.

3. The method of claim 2, wherein the NCPDP network is an NCPDP standard messaging and/or an Internet enabled web interface.

4. The method of claim 1, wherein the computer-implemented adjudication system determines the medical treatment coverage and eligibility by identifying the patient on a patient information database.

5. The method of claim 4, wherein the computer-implemented adjudication system determines the copayment amount information by:
   identifying the medical treatment on a medical treatment database; and then
   identifying the copayment amount information for the medical treatment.

6. The method of claim 5, wherein identifying the copayment amount information for the medical treatment comprises comparing the patient information database to the medical treatment database to determine the copayment amount information that corresponds to a patient's health plan coverage.

7. The method of claim 6, wherein the treatment clinic transmits the health insurance information to the computer-implemented adjudication system by:
   transmitting a financial card number from the treatment clinic to a financial clearing house;
   generating a claim for adjudication at the financial clearing house; and
   transmitting the claim for adjudication from the financial clearing house to the computer-implemented adjudication system.

8. The method of claim 6, wherein the medical treatment coverage, eligibility and copayment amount are directly transmitted from the computer-implemented adjudication system to a retail clinic.

9. The method of claim 6, wherein the copayment amount is transmitted from the computer-implemented adjudication system to a financial clearing house, and then from the financial clearing house to the treatment clinic.

10. The method of claim 1, wherein transmitting the medical treatment coverage, eligibility and copayment amount information from the computer-implemented adjudication system to the treatment clinic comprises displaying cost of payment by the patient for the medical treatment on a retail clinic computer screen.

11. A computer-implemented system for adjudicating a medical treatment transaction, the system comprising one or more processors configured to execute logic code to perform one or more operations comprising:
   receiving a patient request for medical treatment;
   receiving health insurance information associated with the patient request;
   transmitting health insurance information to a computer-implemented adjudication system;
   transmitting medical treatment information associated with the patient request to the computer-implemented adjudication system; and
   receiving medical treatment coverage, eligibility and copayment amount information associated with the medical treatment from the computer-implemented adjudication system, enabling a patient to pay for the requested medical treatment at a point of sale by way of the patient paying a copayment amount to a medical service provider in real time, wherein a computing system at the medical service provider bills a healthcare insurance provider for the requested medical treatment simultaneous to transmitting data specifying the copayment amount paid by the patient, in response to receiving the medical treatment coverage and eligibility information associated with the requested medical treatment.

12. The computer-implemented system of claim 11, wherein the health insurance information and medical treatment information is transmitted from the medical service provider to the computer-implemented adjudication system over a National Council for Prescription Drug Programs (NCPDP) protocol.

13. The computer-implemented system of claim 12, wherein data about the medical treatment coverage, eligibility and copayment amount is transmitted from the computer-implemented adjudication system to the medical service provider over a NCPDP network.

14. The computer-implemented system of claim 12, wherein the NCPDP protocol is an NCPDP standard messaging and/or an Internet enabled web interface.

15. The computer-implemented system of claim 12, wherein the computer-implemented adjudication system determines the medical treatment coverage and eligibility by identifying the patient on a patient information database.

16. A non-transitory computer-readable storage medium comprising at least one program for execution by one or more processors of a first device, the at least one program including instructions which, when executed by the one or more processors, cause the first device to perform operations comprising:

receiving a patient request for medical treatment;

receiving, over a computer network, health insurance information associated with the patient request from a patient information database communicatively coupled to the computer network, the patient information database configured to provide the health insurance information related to a patient;

transmitting, over the computer network, the health insurance information to a computer-implemented adjudication system for processing the health insurance information, the computer-implemented adjudication system configured to process health insurance information and communicatively coupled to the computer network;

transmitting, over the computer network, medical treatment information associated with the patient request to the computer-implemented adjudication system, the medical treatment information received from a medical treatment database and based on a plurality of medical treatments in the medical treatment database, the medical treatment database communicatively coupled to the computer network, the medical treatment database configured to store a plurality of medical treatments including a requested medical treatment and a substitute medical treatment; and receiving, over the computer network, medical treatment coverage, eligibility, and a copayment amount associated with the medical treatment from the computer-implemented adjudication system, such that a medical transaction is adjudicated for the requested medical treatment at a point of sale by way of the patient paying the copayment amount to a treatment clinic in real time, and a computing system at the point of sale bills a healthcare insurance provider for the requested medical treatment simultaneous to transmitting data specifying the copayment amount paid by the patient, in response to receiving the medical treatment coverage and eligibility information associated with the requested medical treatment.

17. The non-transitory computer-readable storage medium of claim 16, wherein the computer network is an NCPDP standard messaging and/or an Internet enabled web interface.

18. The non-transitory computer-readable storage medium of claim 16, wherein the computer-implemented adjudication system determines the medical treatment coverage and eligibility by identifying the patient on the patient information database.

19. The non-transitory computer-readable storage medium of claim 16, wherein controller is further configured to determine the copayment amount by:
   identifying the medical treatment on the medical treatment database; and then
   identifying the copayment amount for the medical treatment.

20. The non-transitory computer-readable storage medium of claim 19, wherein identifying the copayment amount for the medical treatment comprises comparing the patient information database to the medical treatment database to determine the copayment amount that corresponds to a patient's health plan coverage.

* * * * *